(12) United States Patent
Sezi

(10) Patent No.: US 6,866,980 B2
(45) Date of Patent: *Mar. 15, 2005

(54) BIS-O-AMINOPHENOL DERIVATIVES, POLY-O-HYDROXYAMIDES, AND POLYBENZOXAZOLES, USABLE IN PHOTOSENSITIVE COMPOSITIONS, DIELECTRICS, BUFFER COATINGS, AND MICROELECTRONICS

(75) Inventor: Recai Sezi, Röttenbach (DE)

(73) Assignee: Infineon Technologies AG, Munich (DE)

( * ) Notice: Subject to any disclaimer, the term of this patent is extended or adjusted under 35 U.S.C. 154(b) by 105 days.

This patent is subject to a terminal disclaimer.

(21) Appl. No.: 10/244,839

(22) Filed: Sep. 16, 2002

(65) Prior Publication Data

US 2003/0104311 A1 Jun. 5, 2003

(30) Foreign Application Priority Data

Sep. 14, 2001 (DE) .......................... 101 45 463

(51) Int. Cl.$^7$ ..................... C03F 7/004; C07C 215/76
(52) U.S. Cl. ............... 430/270.1; 430/283.1; 528/310; 558/272
(58) Field of Search ............ 430/270.1, 283.1; 528/310; 558/272

(56) References Cited

U.S. PATENT DOCUMENTS

| | | | | |
|---|---|---|---|---|
| 4,845,183 | A | 7/1989 | Mueller et al. | 528/185 |
| 4,939,215 | A | 7/1990 | Mueller et al. | 525/434 |
| 5,053,314 | A | 10/1991 | Yamaoka et al. | 430/270 |
| 2003/0087190 | A1 * | 5/2003 | Sezi | 430/283.1 |
| 2003/0134226 | A1 * | 7/2003 | Sezi | 430/270.1 |

FOREIGN PATENT DOCUMENTS

| EP | 0 317 942 A2 | 5/1989 |
|---|---|---|
| EP | 0 378 156 A2 | 7/1990 |

* cited by examiner

Primary Examiner—Yvette C. Thornton
(74) Attorney, Agent, or Firm—Laurence A. Greenberg; Werner H. Stemer; Gregory L. Mayback

(57) ABSTRACT

Bis-o-aminophenols, which carry on at least one of their hydroxyl groups a tert-butoxy-carbonyl group, can be reacted with dicarboxylic acids to give the corresponding poly-o-hydroxyamides. Following cyclization to the polybenzoxazole, these polymers have a lower dielectric constant than compounds prepared from corresponding poly-o-hydroxyamides which do not carry any tert-butoxycarbonyl group.

22 Claims, No Drawings

US 6,866,980 B2

BIS-O-AMINOPHENOL DERIVATIVES, POLY-O-HYDROXYAMIDES, AND POLYBENZOXAZOLES, USABLE IN PHOTOSENSITIVE COMPOSITIONS, DIELECTRICS, BUFFER COATINGS, AND MICROELECTRONICS

BACKGROUND OF THE INVENTION

Field of the Invention

The invention relates to bis-o-aminophenol derivatives, poly-o-hydroxyamides obtainable from them, and polybenzoxazoles obtained from the poly-o-hydroxyamides. The invention further relates to a photosensitive composition, to the use of the compounds as dielectrics or as buffer coatings, and to a microelectronic component.

In microelectronics, polybenzoxazoles and polyimides possessing high-temperature stability can be used as dielectrics and buffer coatings. Precursors of the polybenzoxazoles, called poly-o-hydroxyamides, also may be made photoreactive by including suitable photoactive components in the formulation. By heat treatment (baking) at temperatures above 250° C., a poly-o-hydroxyamide can be converted into a polybenzoxazole.

The mechanism which is in play during the cyclization of poly-o-hydroxyamides to polybenzoxazoles is depicted schematically below:

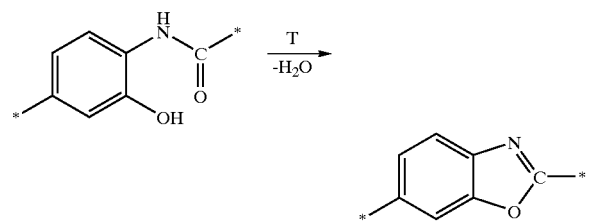

On heating, the o-hydroxyamide undergoes cyclization with elimination of water to form the oxazole.

As well as the thermal and mechanical stabilities, the dielectric constant is an important criterion of these materials, particularly for their use as dielectrics. It must be as small as possible, so that the electrical insulating effect, between the conductor tracks or conductor track planes, for example, is good and the electrical performance of the microelectronic component is enhanced. Polybenzoxazoles and/or poly-o-hydroxy-amides are preferred over polyimides because they generally have a lower dielectric constant than the polyimides.

As compared with polyimides, photostructurable poly-o-hydroxyamides, and/or polybenzoxazoles have the further advantage that they are positively structurable. This leads to a reduced susceptibility to defects, since in the majority of cases only a small portion of the coating need be exposed. Moreover, they are developed in aqueous alkali, whereas the polyimides are usually developed with organic solvents. In the context of production and/or disposal of the materials, it is always advantageous if one component does not consume any organic solvents, which generally have to be disposed of separately.

In order to achieve high resolution, i.e., to be able to produce even small structures, exposure devices are used that operate at low wavelengths: for example, at 248 nm or below. The majority of the buffer coatings used, however, absorb so greatly, even at this wavelength, that adequate exposure of the added photoactive component down into the bottom region of the coating is virtually impossible. This problem can be solved by raising the transparency of the coating, particularly the base polymer of this coating. Accordingly, the transparency of the poly-o-hydroxyamides and/or of the polybenzoxazoles obtained from them is also of particular significance for their suitability in microelectronics.

European Patent Application No. EP 0 317 942, which corresponds to U.S. Pat. Nos. 4,939,215 and 4,845,183, discloses bis-o-aminophenols that are used as monomer units for preparing polymeric benzoxazoles. However, the polymers obtained with these units exhibit very high absorption in the region of 248 nm and below, so that they are suitable only for exposure equipment having a higher wavelength. Moreover, the dielectric constants of the polymers disclosed therein are so high that they cannot be used as dielectrics in microelectronics.

European Patent Application No. EP 0 378 156 A2, which corresponds to U.S. Pat. No. 5,053,314, describes a positively photosensitive polyimide composition. The polymers of the composition are prepared from diamines and tetracarboxylic acids. One of the diamines used is 2,2-bis(3,3'-amino-4,4'-tert-butoxycarbonyloxyphenyl) hexafluoropropane.

SUMMARY OF THE INVENTION

It is accordingly an object of the invention to provide bis-o-aminophenol derivatives, poly-o-hydroxyamides, and polybenzoxazoles, usable in photosensitive compositions, dielectrics, buffer coatings, and microelectronics that overcome the hereinafore-mentioned disadvantages of the heretofore-known devices of this general type. More specifically, the object of the invention is to provide bis-o-aminophenols that are suitable for preparing sufficiently transparent polybenzoxazole precursors that can be used as dielectrics and/or buffer coatings in microelectronic components, and/or which can be photoreactively structured.

The present invention achieves this object by providing bis-o-aminophenol derivatives having the general Formula IIa or IIb

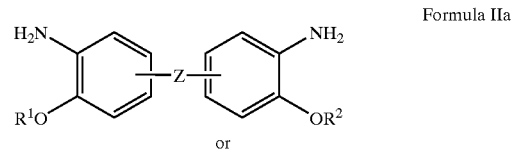

Formula IIa or

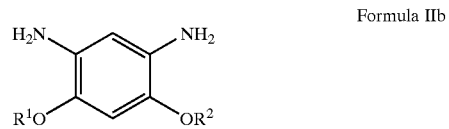

Formula IIb where:

R$^1$ and R$^2$ independently of one another are a hydrogen atom or a tert-butoxycarbonyl group of the Formula I

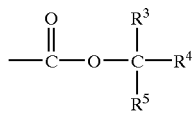

Formula I where $R^3$, $R^4$, and $R^5$ are selected from the following groups: —H; —F; —$(CH_2)_n$—$CH_3$; —$(CF_2)_n$—$CF_3$, with n=0 to 10, provided that at least one of the radicals $R^3$, $R^4$, and $R^5$ is other than hydrogen, and where, in addition, at least one of the radicals $R^1$ and $R^2$ is a tert-butoxycarbonyl group of the Formula I; Z is a carbon-carbon single bond, a carbon-carbon bond shared by two phenyl groups which carry an amino group and an $OR^1$ or $OR^2$ group, a cyclic, branched or straight-chain divalent alkyl radical having from 1 to 20 carbon atoms, a divalent aryl radical having from 6 to 20 carbon atoms or a divalent aralkyl radical whose alkyl group can contain from 1 to 10 carbon atoms and whose aryl group contains from 6 to 20 carbon atoms, it being possible for these radicals as well to be substituted one or more times by halogen, pseudohalogen, or an alkoxy group having from 1 to 10 carbon atoms, in which it is also possible for one or more hydrogen atoms to be substituted by halogen, and where, in addition, these radicals may also be connected via an oxygen atom to the phenyl groups which carry an amino group and an $OR^1$ or $OR^2$ group, or is a divalent heteroatom or a divalent heteroatomic group formed from two or more heteroatoms, or is a divalent silane group, the further valences of the silicon carrying a straight-chain or branched alkyl group having from 1 to 4 carbon atoms, or is a divalent siloxane group having from 2 to 5 silicon atoms, the silicon carrying on its free valences a straight-chain or branched alkyl group having from 1 to 4 carbon atoms, provided that Z is not —$C(CF_3)_2$—.

Examples of suitable heteroatoms include oxygen, sulfur, and nitrogen. The free valence on the nitrogen can be satisfied by hydrogen or by an alkyl group having from 1 to 4 carbon atoms. The phosphorus may be present in a variety of oxidation states and, for example, may also be connected via oxygen to the phenyl rings which carry the amino and the $OR^1$ or $OR^2$ groups.

Z is preferably selected from the group including —O—, —CO—, —S—, —S—S—, —$SO_2$—, —$(CH_2)_m$—, —$(CF_2)_m$ with m=1 to 10,

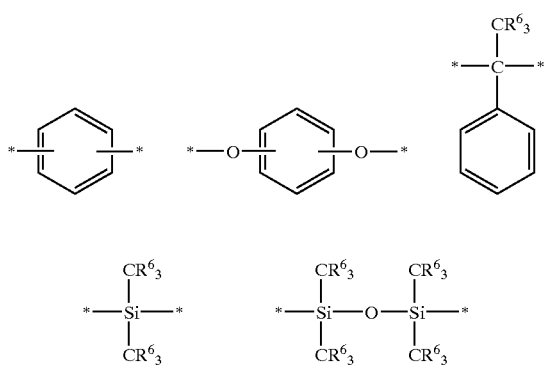

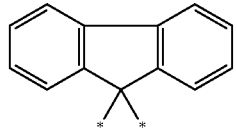

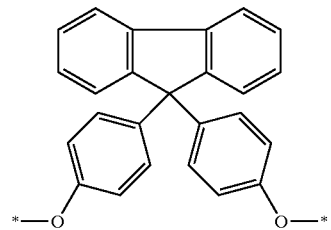

—$C(CR^7_3)_2$—, where $R^6$ can be identical or different and denotes an alkyl radical having 1 or 2 carbon atoms, hydrogen, halogen or pseudohalogen, and $R^7$ can be identical or different and denotes an alkyl radical having 1 or 2 carbon atoms, hydrogen, F, Cl, Br, I or pseudohalogen, at least one of the groups $R^7$ being other than fluorine.

Particularly preferred bis-o-amino compounds are depicted below

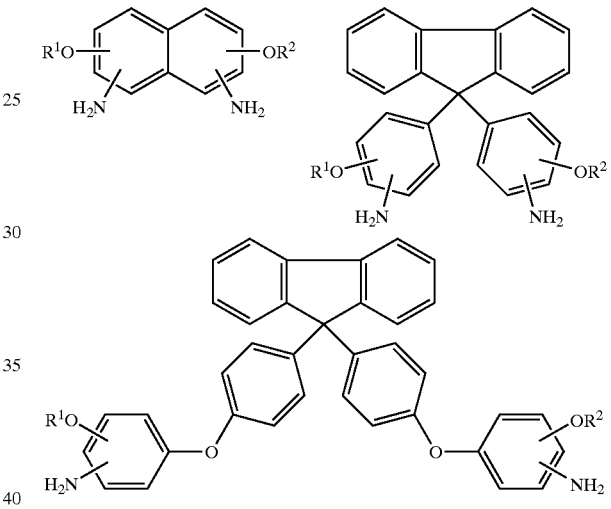

where $R^1$ and $R^2$ are as defined above. The amino group and the $OR^1$ or $OR^2$ group are each positioned ortho to one another.

The bis-o-aminophenol derivatives of the invention carry at least one acid-labile tert-butoxycarbonyl (t-BOC) group of the Formula I and therefore, in particular following their polymerization to the corresponding polybenzoxazole precursor (i.e., a t-BOC-protected poly-o-hydroxyamide), may be used in combination with a photoactive component, a photoacid generator, for example, in a photoactive formulation.

The bis-o-aminophenol derivatives of the invention are obtained by reducing the corresponding nitro compounds.

In one embodiment, the compounds are prepared by reacting the corresponding bis(ortho-nitro-tert-butoxycarbonyloxypheny) compounds with sodium dithionite in the presence of a base, such as sodium hydroxide and/or potassium hydroxide. The bis(ortho-nitro-tert-butoxycarbonyloxyphenyl) compound is preferably dissolved in tetrahydrofuran or dioxane, the sodium dithionite and sodium hydroxide in water, and the two solutions are subsequently reacted with one another. Preferred reaction temperatures are from 0 to 50° C.

The preparation of the bis-o-aminophenol derivatives of the invention is depicted schematically below.

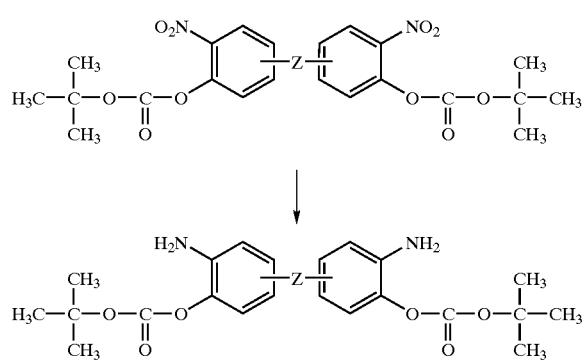

By condensing these bis-o-aminophenol derivatives with dicarboxylic acids or their activated derivatives, such as acid chlorides, it is possible to prepare t-BOC-protected poly-o-hydroxyamides which possess sufficient solubility in solvents such as tetrahydrofuran, alcohols, dioxane or esters, and which possess good film-forming properties. The t-BOC-protected poly-o-hydroxyamides exhibit sufficient transparency at short wavelengths, so making them highly suitable for exposures at 248 nm.

By heating the poly-o-hydroxyamides with elimination of water, carbon dioxide, and isobutene, polybenzoxazoles can be prepared that, surprisingly, exhibit a much lower dielectric constant than the corresponding polymers prepared from monomers without tert-butoxy-carbonyl groups. The dielectric constant of the t-BOC-protected polybenzoxazoles of the invention is generally less than 3, in particular less than 2.7.

The compounds described above are suitable for preparing photosensitive compositions. A photosensitive composition of this kind includes at least one t-BOC-protected poly-o-hydroxyamide, a photoacid, and a solvent, plus a bis-o-aminophenol derivative if desired.

Any compounds that release an acid on irradiation can be used as a photoacid generator. It is advantageous to use onium compounds, as described, for example, in EP 0 955 561 A1, which corresponds to U.S. Pat. No. 6,091,904. Preferred photoacid generators used are ionic compounds in the form of sulfonium salts and iodonium salts.

Solvents that can be used include methoxypropyl acetate, cyclopentanone, cyclohexanone, γ-butyro-lactone, ethyl lactate, diethylene glycol diethyl ether, diethylene glycol dimethyl ether, or a mixture of at least two of said solvents. In general, however, all customary solvents or mixtures thereof may be used provided the components of the photosensitive composition can be dissolved therein to give a clear, homogeneous, and storage-stable solution—provided that they ensure good coating quality when the substrate is coated.

The compounds of the invention are very suitable as dielectrics or as buffer coatings in a microelectronic component. Therefore, the invention further provides a microelectronic component that includes a material based on the compounds described above.

In contrast to the analogous poly-o-hydroxyamides with free hydroxyl groups prepared from the unprotected bis-o-aminophenols, the t-BOC-protected poly-o-hydroxy-amides prepared from the novel bis-o-aminophenols of the Formulae IIa and IIb can be structured without problems using short-wavelength light, at 248 nm, for example, by lithographic techniques.

Other features that are considered as characteristic for the invention are set forth in the appended claims.

Although the invention is illustrated and described herein as embodied in bis-o-aminophenol derivatives, poly-o-hydroxyamides, and polybenzoxazoles, usable in photosensitive compositions, dielectrics, buffer coatings, and microelectronics, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the examples.

DESCRIPTION OF THE PREFERRED EMBODIMENTS

Referring now to the examples, classes of compounds represent the preparation both of their simple derivatives and of those derivatives where the position of the substituents or the substituents themselves have been changed on at least one of the aromatic rings.

The bis-o-aminophenols with tert-butoxycarbonyl protective groups are prepared from the corresponding nitrophenols whose hydroxyl groups have been protected with tert-butoxycarbonyl groups.

EXAMPLE 1

Preparation of 2,2-bis(3,3'-amino-4,4'-tert-butoxycarbonyloxyphenyl)hexafluoropropane (see EP 0 378 156 A2)

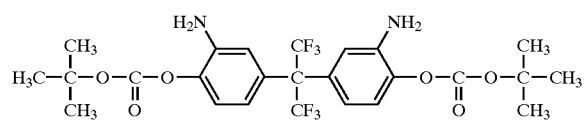

In a three-neck round-bottom flask, 26.1 g (0.15 mol) of sodium dithionite ($Na_2S_2O_4$) and 12 g (0.3 mol) of sodium hydroxide (NaOH) are dissolved under nitrogen in 210 ml of distilled water, with stirring. Then a solution of 18.8 g (0.03 mol) of 2,2'-bis(3,3'-nitro-4,4'-tert-butoxycarbonyloxyphenyl)hexafluoropropane in 260 ml of tetrahydrofuran (THF) is introduced slowly, dropwise into the first solution at room temperature and the mixture is stirred at room temperature for 6 hours. Approximately 150 ml of THF are then distilled off under reduced pressure in a rotary evaporator at 40° C. and the remaining reaction solution is extracted with three times 80 ml of ethyl acetate. The combined ethyl acetate extracts are first washed with twice 50 ml of distilled water and then with three times 100 ml of 1% strength hydrochloric acid (in water), the temperature of the acid at the beginning being not more than 10° C. The combined hydrochloric acid extracts are neutralized with 1% strength sodium hydroxide in water. The turbid solution is subsequently stored in a refrigerator.

After 48 hours the solution is filtered through a folded filter and washed with three times 50 ml of distilled water and the solid product is dried in a drying cabinet at 40° C./100 mbar for 72 hours.

10.3 g of product are obtained.

Elemental Analysis

The compound was determined to have to following elemental composition: 53.1% C; 5.1% H; 4.9% N.

Mass Spectrum

A molecule peak was found at 566.

EXAMPLE 2

Preparation of 3,3'-amino-4,4'-tert-butoxy-carbonyloxy-biphenyl

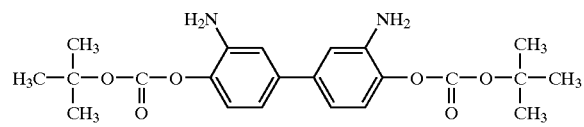

The synthesis is carried out in the same way as described in Example 1 but in this case using as starting material 14.3 g (0.03 mol) of 3,3'-nitro-4,4'-tert-butoxycarbonyloxy-biphenyl and using dioxane instead of THF as solvent. All other worksteps and conditions are the same.

18.2 g of product are obtained.

Elemental Analysis

The compound had the following elemental composition: 63.3% C; 6.9% H; 6.6% N.

Mass Spectrum

A molecule peak was found at 416.

EXAMPLE 3

Preparation of 3,3'-amino-4,4'-tert-butoxy-carbonyloxy-diphenyl ether

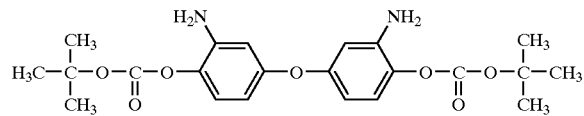

The synthesis is carried out in the same way as described in Example 1 but in this case using as starting material 14.8 g (0.03 mol) of 3,3'-nitro-4,4'-hydroxydiphenyl ether. All other worksteps and conditions are the same.

9.6 g of product are obtained.

Elemental Analysis

The compound had the following elemental composition: 61.0% C; 6.4% H; 6.6% N.

Mass Spectrum

Molecule peak was found at 432.

EXAMPLE 4

Preparation of 9,9-bis(3-amino-4-tert-butoxycarbonyloxy-phenyl)fluorene

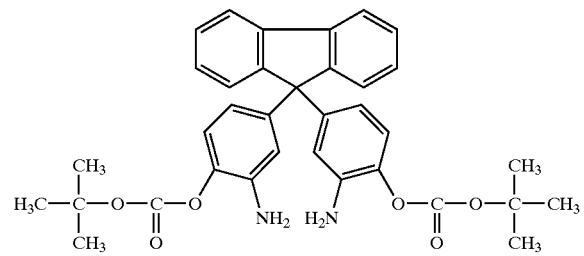

The synthesis is carried out in the same way as described in Example 1 but using here as starting material 19.2 g (0.03 mol) of 9,9-bis(3-nitro-4-tert-butoxycarbonyloxyphenyl) fluorene. All other conditions and worksteps are the same.

14.2 g of product are obtained.

Elemental Analysis

The compound had the following elemental composition: 72.4% C; 6.1% H; 4.8% N.

Mass Spectrum

A molecule peak was found at 580.

I claim:

1. A bis-o-aminophenol derivative, comprising:

a bis-o-aminophenol having a formula selected from the group consisting of Formula IIa and IIb

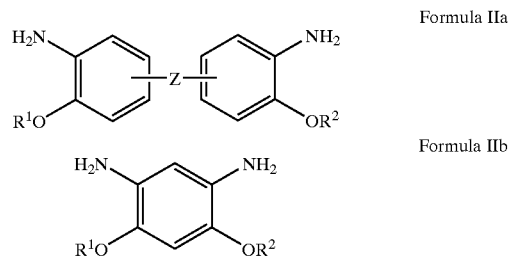

Formula IIa

Formula IIb where:

$R^1$ and $R^2$ are substituents independently selected from the group consisting of a hydrogen atom and a tert-butoxycarbonyl group having a Formula I

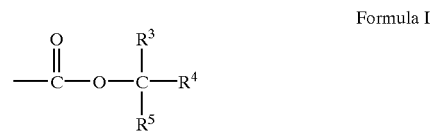

Formula I where $R^3$, $R^4$, and $R^5$ are substituents selected from the group consisting of: —H; —F; —$(CH_2)_n$—$CH_3$; —$(CF_2)_n$—$CF_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I; and Z is a substituent selected from the group consisting of a carbon-carbon single bond, a carbon-carbon bond shared by said two phenyl groups carrying said amino group and one of said $OR^1$ group and said $OR^2$ group, a divalent alkyl radical having from 1 to 20 carbon atoms, a divalent aryl radical having from 6 to 20 carbon atoms, and a divalent aralkyl radical having an alkyl group.

2. The bis-o-aminophenol derivative according to claim 1, if said substituent of Z is a divalent alkyl, said divalent alkyl is cyclic.

3. The bis-o-aminophenol derivative according to claim 1, if said substituent of Z is a divalent alkyl, said divalent alkyl is branched.

4. The bis-o-aminophenol derivative according to claim 1, if said substituent of Z is a divalent alkyl, said divalent alkyl is a straight-chain.

5. The bis-o-aminophenol derivative according to claim 1, wherein, if said substituent of Z is a divalent aralkyl, said divalent aralkyl contains from 1 to 10 carbon atoms.

6. The bis-o-aminophenol derivative according to claim 1, wherein, if said substituent of Z is a divalent aralkyl, said alkyl group of said divalent aralkyl contains from 6 to 20 carbon atoms.

7. The bis-o-aminophenol derivative according to claim 1, wherein said substituent of Z has a substitutent selected from the group consisting of halogen, pseudohalogen, and an alkoxy group having from 1 to 10 carbon atoms.

8. The bis-o-aminophenol derivative according to claim 7, wherein, if said substituent is an alkoxy group, said alkoxy group has at least one hydrogen atom substituted by a halogen.

9. The bis-o-aminophenol derivative according to claim 1, wherein, if said substituent of Z is a carbon-carbon bond shared by said two phenyl groups carrying said amino group and one of said $OR^1$ group and said $OR^2$ group, said phenyl groups are connected by a connector selected from the group consisting of an oxygen atom to said phenyl groups, a divalent heteroatom, a divalent heteroatomic group formed from two or more heteroatoms, a divalent silane group having a silicone with further valences carrying an alkyl group having from 1 to 4 carbon atoms, a divalent siloxane group having from 2 to 5 silicon atoms with free valances carrying an alkyl group having from 1 to 4 carbon atoms, provided that Z is not $—C(CF_3)_2—$.

10. The bis-o-aminophenol derivative according to claim 9, wherein, if said connector is a divalent silane group, said alkyl group is a straight-chain.

11. The bis-o-aminophenol derivative according to claim 9, wherein, if said connector is a divalent silane group, said alkyl group is branched.

12. The bis-o-aminophenol derivative according to claim 9, wherein, if said connector is a divalent siloxane group, said alkyl group is a straight-chain.

13. The bis-o-aminophenol derivative according to claim 9, wherein, if said connector is a divalent siloxane group, said alkyl group is branched.

14. A bis-o-aminophenol derivative, comprising:
a bis-o-aminophenol having a formula selected from the group consisting of Formula IIa and IIb

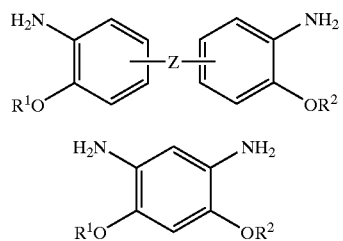

Formula IIa

Formula IIb where:
$R^1$ and $R^2$ are substituents independently selected from the group consisting of a hydrogen atom and a tert-butoxycarbonyl group having a Formula I

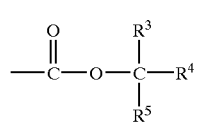

Formula I where $R^3$, $R^4$, and $R^5$ are substituents selected from the group consisting of: —H; —F; —$(CH_2)_n$—$CH_3$; —$(CF_2)_n$—$CF_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I; and Z is a substituent selected from the group consisting of —O—, —CO—, —S—, —S—S—, —$SO_2$—, —$(CH_2)_m$—, —$(CF_2)_m$ with m=1 to 10,

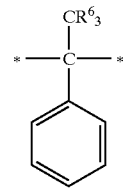
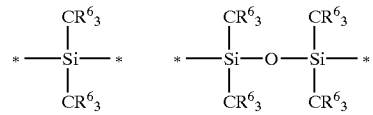

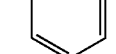

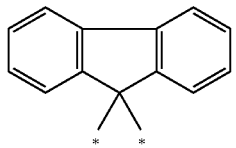 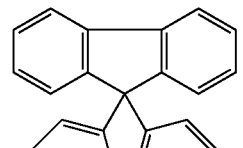

—$C(CR^7{}_3)_2$—, where $R^6$ is independently selected and denotes an alkyl radical having from 1 or 2 carbon atoms, hydrogen, and at least one of a halogen and a pseudohalogen, and where $R^7$ is independently selected and denotes an alkyl radical having from 1 to 2 carbon atoms, and at least one of a hydrogen, a F, a Cl, a Br, an I, and a pseudohalogen, and at least one $R^7$ is other than fluorine.

15. A poly-o-hydroxyamide, comprising:
tert-butoxycarbonyl groups having a Formula I

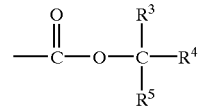

Formula I where $R^3$, $R^4$, and $R^5$ are substituents selected from the group consisting of: —H; —F; —$(CH_2)_n$—$CH_3$; —$(CF_2)_n$—$CF_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I;

said tert-butoxycarbonyl groups being obtained, with at least one of a dicarboxylic acid or an activated derivative of a dicarboxylic acid, by condensing a bis-o-aminophenol derivative including:
a bis-o-aminophenol having a formula selected from the group consisting of Formula IIa and IIb

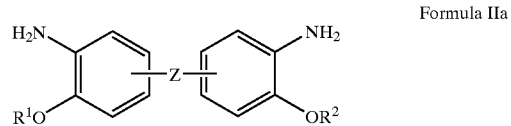

Formula IIa

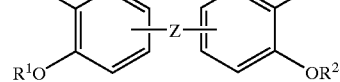

-continued

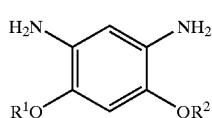
Formula IIb where:
R$^1$ and R$^2$ are substituents independently selected from the group consisting of a hydrogen atom and a tert-butoxycarbonyl group having said Formula I; and
Z is a substituent selected from the group consisting of a carbon-carbon single bond, a carbon-carbon bond shared by said two phenyl groups carrying said amino group and one of said OR$^1$ group and said OR$^2$ group, a divalent alkyl radical having from 1 to 20 carbon atoms, a divalent aryl radical having from 6 to 20 carbon atoms, and a divalent aralkyl radical having an alkyl group.

16. A poly-o-hydroxyamide, comprising:
tert-butoxycarbonyl groups having a Formula I

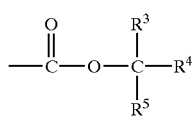
Formula I where R$^3$, R$^4$, and R$^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals R$^3$, R$^4$, and R$^5$ is other than hydrogen, and where at least one of the substituents R$^1$ and R$^2$ is a tert-butoxycarbonyl group of the Formula I;
said tert-butoxycarbonyl groups being obtained, with at least one of a dicarboxylic acid or an activated derivative of a dicarboxylic acid, by condensing a bis-o-aminophenol derivative including:
a bis-o-aminophenol having a formula selected from the group consisting of Formula IIa and IIb

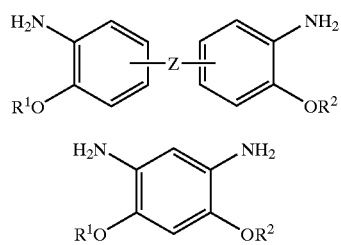
Formula IIa

Formula IIb where:
R$^1$ and R$^2$ are substituents independently selected from the group consisting of a hydrogen atom and a tert-butoxycarbonyl group having said Formula I; and
Z is a substituent selected from the group consisting of —O—, —CO—, —S—, —S—S—, —SO$_2$—, —(CH$_2$)$_m$—, —(CF$_2$)$_m$ with m=1 to 10,

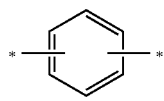 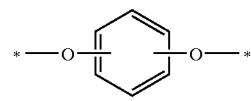

-continued

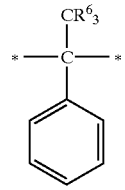

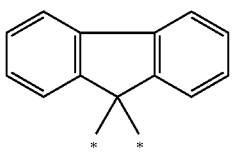

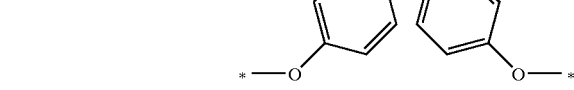

—C(CR$^7$$_3$)$_2$—, where R$^6$ is independently selected and denotes an alkyl radical having from 1 or 2 carbon atoms, hydrogen, and at least one of a halogen and a pseudohalogen, and where R$^7$ is independently selected and denotes an alkyl radical having from 1 to 2 carbon atoms, and at least one of a hydrogen, a F, a Cl, a Br, an I, and a pseudohalogen, and at least one R$^7$ is other than fluorine.

17. A polybenzoxazole, comprising:
poly-o-hydroxyamide including tert-butoxycarbonyl groups having a Formula I

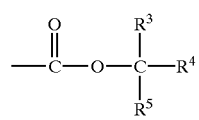
Formula I where R$^3$, R$^4$, and R$^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals R$^3$, R$^4$, and R$^5$ is other than hydrogen, and where at least one of the substituents R$^1$ and R$^2$ is a tert-butoxycarbonyl group of the Formula I;
said tert-butoxycarbonyl groups being obtained, with at least one of a dicarboxylic acid or an activated derivative of a dicarboxylic acid, by condensing a bis-o-aminophenol derivative including:
a bis-o-aminophenol having a formula selected from the group consisting of Formula IIa and IIb

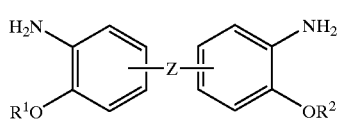
Formula IIa

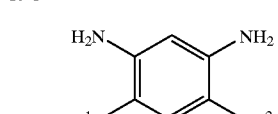
Formula IIb where:
R$^1$ and R$^2$ are substituents independently selected from the group consisting of a hydrogen atom and a tert-butoxycarbonyl group having said Formula I; and Z is a substituent selected from the group consisting of a carbon-carbon single bond, a carbon-carbon bond shared by said two phenyl groups carrying said amino group and one of said $OR^1$ group and said $OR^2$ group, a divalent alkyl radical having from 1 to 20 carbon atoms, a divalent aryl radical having from 6 to 20 carbon atoms, and a divalent aralkyl radical having an alkyl group.

18. A polybenzoxazole, comprising:

a poly-o-hydroxyamide including tert-butoxycarbonyl groups having a Formula I

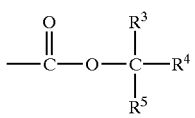

Formula I where $R^3$, $R^4$, and $R^5$ are substituents selected from the group consisting of: —H; —F; —$(CH_2)_n$—$CH_3$; —$(CF_2)_n$—$CF_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I;

said tert-butoxycarbonyl groups being obtained, with at least one of a dicarboxylic acid or an activated derivative of a dicarboxylic acid, by condensing a bis-o-aminophenol derivative including:

a bis-o-aminophenol having a formula selected from the group consisting of Formula IIa and IIb

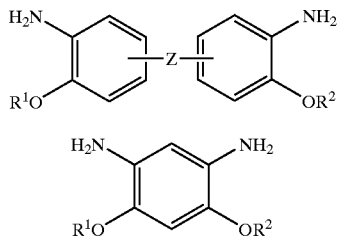

Formula IIa

Formula IIb where:

$R^1$ and $R^2$ are substituents independently selected from the group consisting of a hydrogen atom and a tert-butoxycarbonyl group having said Formula I; and Z is a substituent selected from the group consisting of —O—, —CO—, —S—, —S—S—, —$SO_2$—, —$(CH_2)_m$—, —$(CF_2)_m$ with m=1 to 10,

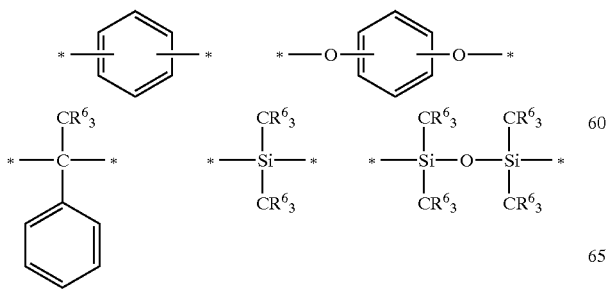

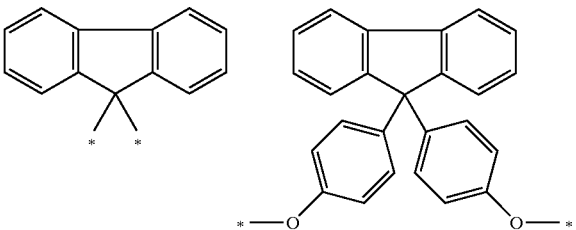

—$C(CR^7{}_3)_2$—, where $R^6$ is independently selected and denotes an alkyl radical having from 1 or 2 carbon atoms, hydrogen, and at least one of a halogen and a pseudohalogen, and where $R^7$ is independently selected and denotes an alkyl radical having from 1 to 2 carbon atoms, and at least one of a hydrogen, a F, a Cl, a Br, an I, and a pseudohalogen, and at least one $R^7$ is other than fluorine.

19. A photosensitive composition, comprising:

a photoacid;

a solvent; and a compound selected from the group consisting of:

a bis-o-aminophenol derivative including a bis-o-aminophenol having a formula selected from the group consisting of Formula IIa and IIb

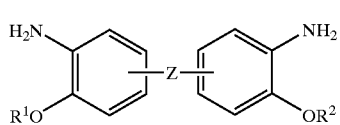

Formula IIa

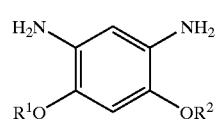

Formula IIb where:

$R^1$ and $R^2$ are substituents independently selected from the group consisting of a hydrogen atom and a tert-butoxycarbonyl group having a Formula I

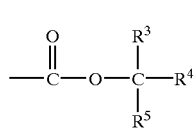

Formula I where $R^3$, $R^4$, and $R^5$ are substituents selected from the group consisting of: —H; —F; —$(CH_2)_n$—$CH_3$; —$(CF_2)_n$—$CF_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I; and Z is a substituent selected from the group consisting of a carbon-carbon single bond, a carbon-carbon bond shared by said two phenyl groups carrying said amino group and one of said $OR^1$ group and said $OR^2$ group, a divalent alkyl radical having from 1 to 20 carbon atoms, a divalent aryl radical having from 6 to 20 carbon atoms, and a divalent aralkyl radical having an alkyl group;

a bis-o-aminophenol derivative including a bis-o-aminophenol having a formula selected from the group consisting of Formula IIa and IIb

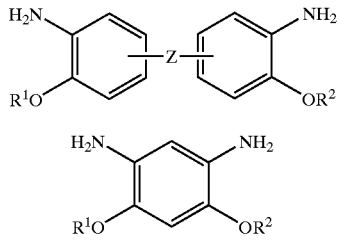

Formula IIa

Formula IIb where:
R$^1$ and R$^2$ are substituents independently selected from the group consisting of a hydrogen atom and a tert-butoxycarbonyl group having a Formula I

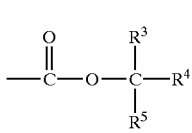

Formula I where R$^3$, R$^4$, and R$^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals R$^3$, R$^4$, and R$^5$ is other than hydrogen, and where at least one of the substituents R$^1$ and R$^2$ is a tert-butoxycarbonyl group of the Formula I; and Z is a substituent selected from the group consisting of —O—, —CO—, —S—, —S—S—, —SO$_2$—, —(CH$_2$)$_m$—, —(CF$_2$)$_m$ with m=1 to 10,

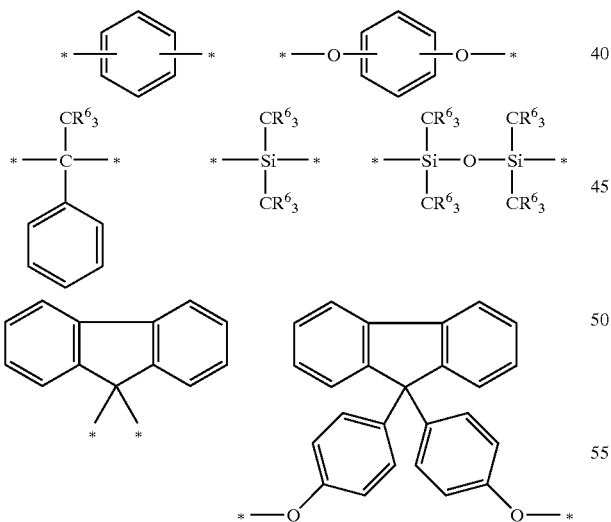

—C(CR$^7$$_3$)$_2$—, where R$^6$ is independently selected and denotes an alkyl radical having from 1 or 2 carbon atoms, hydrogen, and at least one of a halogen and a pseudohalogen, and where R$^7$ is independently selected and denotes an alkyl radical having from 1 to 2 carbon atoms, and at least one of a hydrogen, a F, a Cl, a Br, an I, and a pseudohalogen, and at least one R$^7$ is other than fluorine;

a poly-o-hydroxyamide including tert-butoxycarbonyl groups having a Formula I

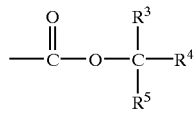

Formula I where R$^3$, R$^4$, and R$^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals R$^3$, R$^4$, and R$^5$ is other than hydrogen, and where at least one of the substituents R$^1$ and R$^2$ is a tert-butoxycarbonyl group of the Formula I;

said tert-butoxycarbonyl groups being obtained, with at least one of a dicarboxylic acid or an activated derivative of a dicarboxylic acid, by condensing a bis-o-aminophenol derivative including:

a bis-o-aminophenol having a formula selected from the group consisting of Formula IIa and IIb

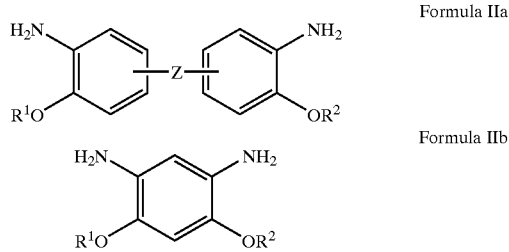

Formula IIa

Formula IIb where:
R$^1$ and R$^2$ are substituents independently selected from the group consisting of a hydrogen atom and a tert-butoxycarbonyl group having said Formula I; and Z is a substituent selected from the group consisting of a carbon-carbon single bond, a carbon-carbon bond shared by said two phenyl groups carrying said amino group and one of said OR$^1$ group and said OR$^2$ group, a divalent alkyl radical having from 1 to 20 carbon atoms, a divalent aryl radical having from 6 to 20 carbon atoms, and a divalent aralkyl radical having an alkyl group; and a poly-o-hydroxyamide including tert-butoxycarbonyl groups having a Formula I

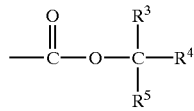

Formula I where R$^3$, R$^4$, and R$^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals R$^3$, R$^4$, and R$^5$ is other than hydrogen, and where at least one of the substituents R$^1$ and R$^2$ is a tert-butoxycarbonyl group of the Formula I;

said tert-butoxycarbonyl groups being obtained, with at least one of a dicarboxylic acid or an activated derivative of a dicarboxylic acid, by condensing a bis-o-aminophenol derivative including:

a bis-o-aminophenol having a formula selected from the group consisting of Formula IIa and IIb

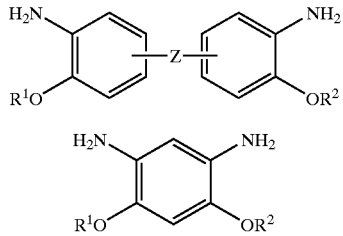

Formula IIa

Formula IIb

Formula IIb
where:
$R^1$ and $R^2$ are substituents independently selected from the group consisting of a hydrogen atom and a tert-butoxycarbonyl group having said Formula I; and
Z is a substituent selected from the group consisting of —O—, —CO—, —S—, —S—S—, —SO$_2$—, —(CH$_2$)$_m$—, —(CF$_2$)$_m$ with m=1 to 10,

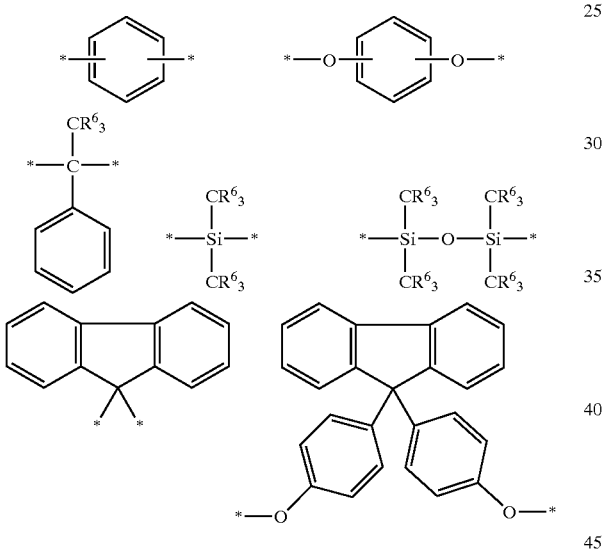

—C(CR$^7{}_3$)$_2$—, where $R^6$ is independently selected and denotes an alkyl radical having from 1 or 2 carbon atoms, hydrogen, and at least one of a halogen and a pseudohalogen, and where $R^7$ is independently selected and denotes an alkyl radical having from 1 to 2 carbon atoms, and at least one of a hydrogen, a F, a Cl, a Br, an I, and a pseudohalogen, and at least one $R^7$ is other than fluorine.

20. A dielectric for coating a microelectronic component, comprising:
a compound selected from the group consisting of:
a bis-o-aminophenol derivative including a bis-o-aminophenol having a formula selected from the group consisting of Formula IIa and IIb

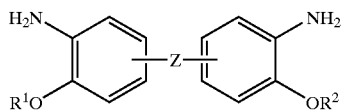

Formula IIa

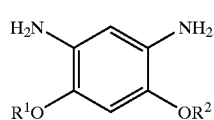

Formula IIb where:
$R^1$ and $R^2$ are substituents independently selected from the group consisting of a hydrogen atom and a tert-butoxycarbonyl group having a Formula I

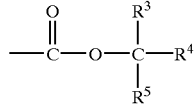

Formula I where $R^3$, $R^4$, and $R^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I; and
Z is a substituent selected from the group consisting of a carbon-carbon single bond, a carbon-carbon bond shared by said two phenyl groups carrying said amino group and one of said OR$^1$ group and said OR$^2$ group, a divalent alkyl radical having from 1 to 20 carbon atoms, a divalent aryl radical having from 6 to 20 carbon atoms, and a divalent aralkyl radical having an alkyl group;
a bis-o-aminophenol derivative including a bis-o-aminophenol having a formula selected from the group consisting of Formula IIa and IIb

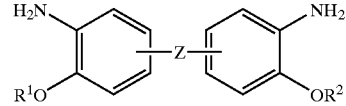

Formula IIa

Formula IIb where:
$R^1$ and $R^2$ are substituents independently selected from the group consisting of a hydrogen atom and a tert-butoxycarbonyl group having a Formula I

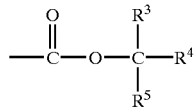

Formula I where $R^3$, $R^4$, and $R^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I; and Z is a substituent selected from the group consisting of —O—, —CO—, —S—, —S—S—, —SO$_2$—, —(CH$_2$)$_m$—, —(CF$_2$)$_m$ with m=1 to 10,

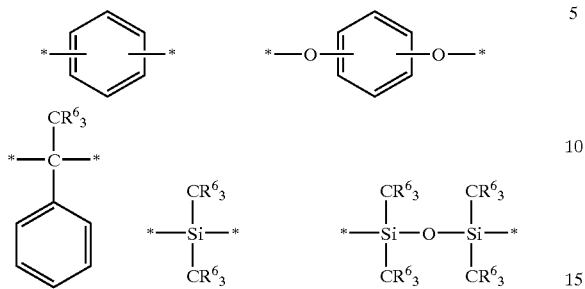

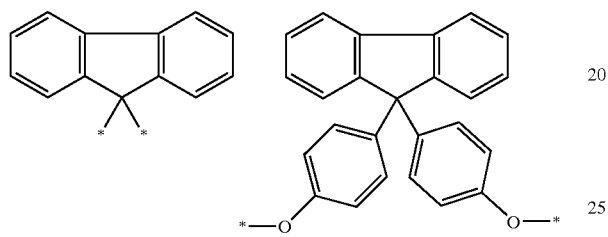

—C(CR$^7$$_3$)$_2$—, where R$^6$ is independently selected and denotes an alkyl radical having from 1 or 2 carbon atoms, hydrogen, and at least one of a halogen and a pseudohalogen, and where R$^7$ is independently selected and denotes an alkyl radical having from 1 to 2 carbon atoms, and at least one of a hydrogen, a F, a Cl, a Br, an I, and a pseudohalogen, and at least one R$^7$ is other than fluorine;

a poly-o-hydroxyamide including tert-butoxycarbonyl groups having a Formula I

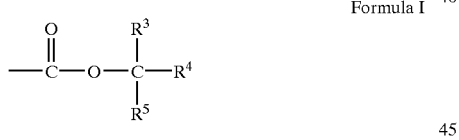

Formula I where R$^3$, R$^4$, and R$^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals R$^3$, R$^4$, and R$^5$ is other than hydrogen, and where at least one of the substituents R$^1$ and R$^2$ is a tert-butoxycarbonyl group of the Formula I;

said tert-butoxycarbonyl groups being obtained, with at least one of a dicarboxylic acid or an activated derivative of a dicarboxylic acid, by condensing a bis-o-aminophenol derivative including:

a bis-o-aminophenol having a formula selected from the group consisting of Formula IIa and IIb

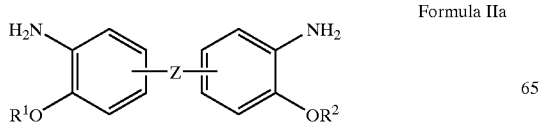

Formula IIa

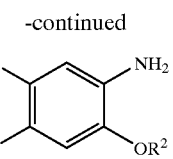

Formula IIb where:
R$^1$ and R$^2$ are substituents independently selected from the group consisting of a hydrogen atom and a tert-butoxycarbonyl group having said Formula I; and Z is a substituent selected from the group consisting of a carbon-carbon single bond, a carbon-carbon bond shared by said two phenyl groups carrying said amino group and one of said OR$^1$ group and said OR$^2$ group, a divalent alkyl radical having from 1 to 20 carbon atoms, a divalent aryl radical having from 6 to 20 carbon atoms, and a divalent aralkyl radical having an alkyl group; and a poly-o-hydroxyamide including tert-butoxycarbonyl groups having a Formula I

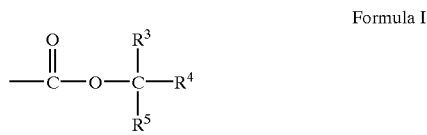

Formula I where R$^3$, R$^4$, and R$^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals R$^3$, R$^4$, and R$^5$ is other than hydrogen, and where at least one of the substituents R$^1$ and R$^2$ is a tert-butoxycarbonyl group of the Formula I;

said tert-butoxycarbonyl groups being obtained, with at least one of a dicarboxylic acid or an activated derivative of a dicarboxylic acid, by condensing a bis-o-aminophenol derivative including:

a bis-o-aminophenol having a formula selected from the group consisting of Formula IIa and IIb

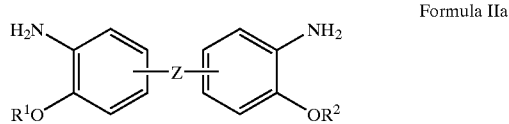

Formula IIa

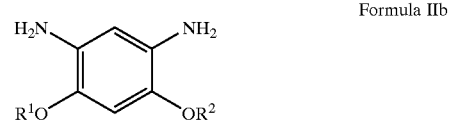

Formula IIb where:
R$^1$ and R$^2$ are substituents independently selected from the group consisting of a hydrogen atom and a tert-butoxycarbonyl group having said Formula I; and Z is a substituent selected from the group consisting of —O—, —CO—, —S—, —S—S—, —SO$_2$—, —(CH$_2$)$_m$—, —(CF$_2$)$_m$ with m=1 to 10,

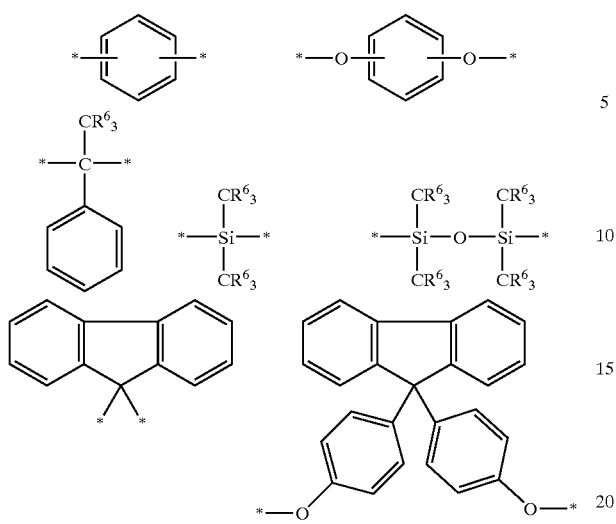

—C(CR⁷₃)₂—, where $R^6$ is independently selected and denotes an alkyl radical having from 1 or 2 carbon atoms, hydrogen, and at least one of a halogen and a pseudohalogen, and where $R^7$ is independently selected and denotes an alkyl radical having from 1 to 2 carbon atoms, and at least one of a hydrogen, a F, a Cl, a Br, an I, and a pseudohalogen, and at least one $R^7$ is other than fluorine.

21. A buffer for coating a microelectronic component, comprising:

a compound selected from the group consisting of:

a bis-o-aminophenol derivative including a bis-o-aminophenol having a formula selected from the group consisting of Formula IIa and IIb

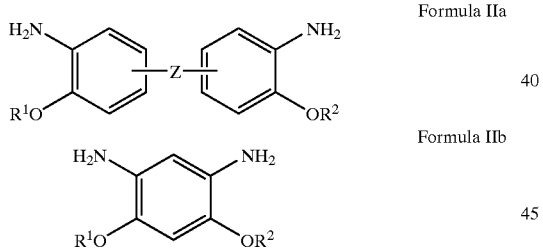

Formula IIa

Formula IIb where:

$R^1$ and $R^2$ are substituents independently selected from the group consisting of a hydrogen atom and a tert-butoxycarbonyl group having a Formula I

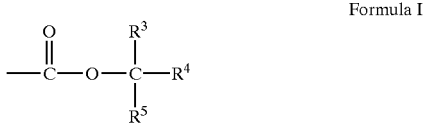

Formula I where $R^3$, $R^4$, and $R^5$ are substituents selected from the group consisting of: —H; —F; —(CH₂)ₙ—CH₃; —(CF₂)ₙ—CF₃, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I; and Z is a substituent selected from the group consisting of a carbon-carbon single bond, a carbon-carbon bond shared by said two phenyl groups carrying said amino group and one of said OR¹ group and said OR² group, a divalent alkyl radical having from 1 to 20 carbon atoms, a divalent aryl radical having from 6 to 20 carbon atoms, and a divalent aralkyl radical having an alkyl group;

a bis-o-aminophenol derivative including a bis-o-aminophenol having a formula selected from the group consisting of Formula IIa and IIb

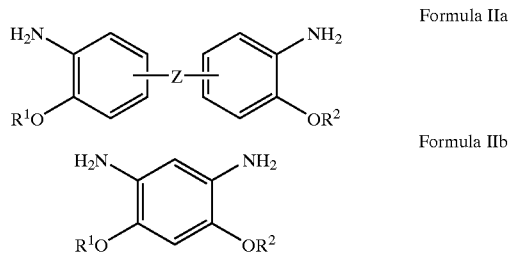

Formula IIa

Formula IIb where:

$R^1$ and $R^2$ are substituents independently selected from the group consisting of a hydrogen atom and a tert-butoxycarbonyl group having a Formula I

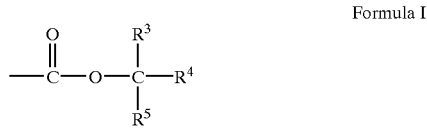

Formula I where $R^3$, $R^4$, and $R^5$ are substituents selected from the group consisting of: —H; —F; —(CH₂)ₙ—CH₃; —(CF₂)ₙ—CF₃, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I; and Z is a substituent selected from the group consisting of —O—, —CO—, —S—, —S—S—, —SO₂—, —(CH₂)ₘ—, —(CF₂)ₘ with m=1 to 10,

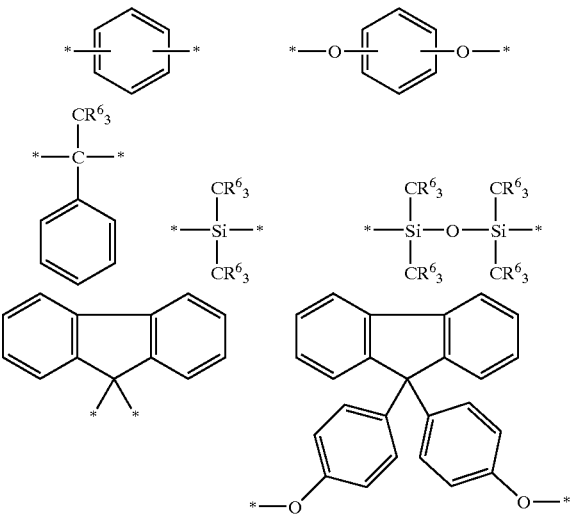

—C(CR⁷₃)₂—, where $R^6$ is independently selected and denotes an alkyl radical having from 1 or 2 carbon atoms, hydrogen, and at least one of a halogen and a pseudohalogen, and where $R^7$ is independently selected and denotes an alkyl radical having from 1 to 2 carbon atoms, and at least one of a hydrogen, a F, a Cl, a Br, an I, and a pseudohalogen, and at least one $R^7$ is other than fluorine;

a poly-o-hydroxyamide including tert-butoxycarbonyl groups having a Formula I

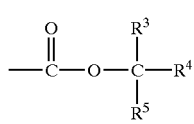

Formula I where $R^3$, $R^4$, and $R^5$ are substituents selected from the group consisting of: —H; —F; —$(CH_2)_n$—$CH_3$; —$(CF_2)_n$—$CF_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I;

said tert-butoxycarbonyl groups being obtained, with at least one of a dicarboxylic acid or an activated derivative of a dicarboxylic acid, by condensing a bis-o-aminophenol derivative including:

a bis-o-aminophenol having a formula selected from the group consisting of Formula IIa and IIb

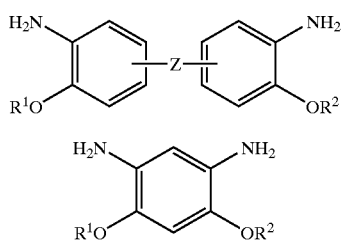

Formula IIa

Formula IIb where:

$R^1$ and $R^2$ are substituents independently selected from the group consisting of a hydrogen atom and a tert-butoxycarbonyl group having said Formula I; and Z is a substituent selected from the group consisting of a carbon-carbon single bond, a carbon-carbon bond shared by said two phenyl groups carrying said amino group and one of said $OR^1$ group and said $OR^2$ group, a divalent alkyl radical having from 1 to 20 carbon atoms, a divalent aryl radical having from 6 to 20 carbon atoms, and a divalent aralkyl radical having an alkyl group; and a poly-o-hydroxyamide including tert-butoxycarbonyl groups having a Formula I

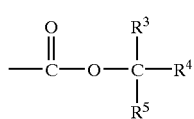

Formula I where $R^3$, $R^4$, and $R^5$ are substituents selected from the group consisting of: —H; —F; —$(CH_2)_n$—$CH_3$; —$(CF_2)_n$—$CF_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I;

said tert-butoxycarbonyl groups being obtained, with at least one of a dicarboxylic acid or an activated derivative of a dicarboxylic acid, by condensing a bis-o-aminophenol derivative including:

a bis-o-aminophenol having a formula selected from the group consisting of Formula IIa and IIb

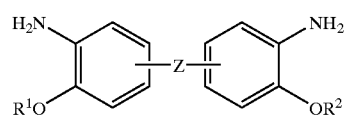

Formula IIa

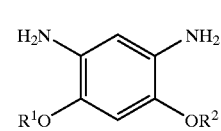

Formula IIb where:

$R^1$ and $R^2$ are substituents independently selected from the group consisting of a hydrogen atom and a tert-butoxycarbonyl group having said Formula I; and Z is a substituent selected from the group consisting of —O—, —CO—, —S—, —S—S—, —$SO_2$—, —$(CH_2)_m$—, —$(CF_2)_m$ with m=1 to 10,

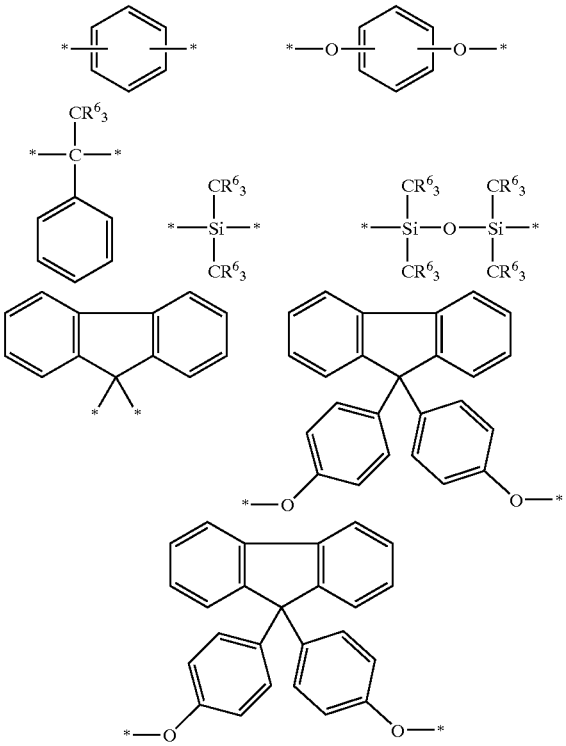

—$C(CR^7_3)_2$—, where $R^6$ is independently selected and denotes an alkyl radical having from 1 or 2 carbon atoms, hydrogen, and at least one of a halogen and a pseudohalogen, and where $R^7$ is independently selected and denotes an alkyl radical having from 1 to 2 carbon atoms, and at least one of a hydrogen, a F, a Cl, a Br, an I, and a pseudohalogen, and at least one $R^7$ is other than fluorine.

22. A microelectronic assembly, comprising:

a microelectronic component; and a material coating said microelectronic component based on a compound selected from the group consisting of:

a bis-o-aminophenol derivative including a bis-o-aminophenol having a formula selected from the group consisting of Formula IIa and IIb

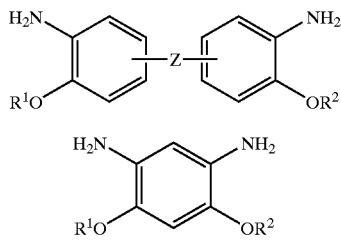

Formula IIa

Formula IIb where:

$R^1$ and $R^2$ are substituents independently selected from the group consisting of a hydrogen atom and a tert-butoxycarbonyl group having a Formula I

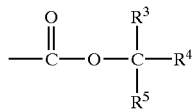

Formula I where $R^3$, $R^4$, and $R^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I; and Z is a substituent selected from the group consisting of a carbon-carbon single bond, a carbon-carbon bond shared by two phenyl groups carrying an amino group and a further substituent selected from the group consisting of an OR$^1$ group, an OR$^2$ group, a divalent alkyl radical having from 1 to 20 carbon atoms, a divalent aryl radical having from 6 to 20 carbon atoms, and a divalent aralkyl radical having an alkyl group, a bis-o-aminophenol derivative including a bis-o-aminophenol having a formula selected from the group consisting of Formula IIa and IIb

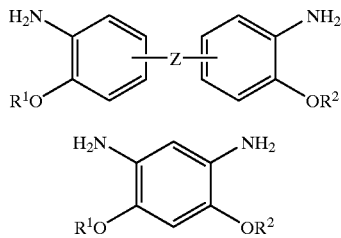

Formula IIa

Formula IIb where:

$R^1$ and $R^2$ are substituents independently selected from the group consisting of a hydrogen atom and a tert-butoxycarbonyl group having a Formula I

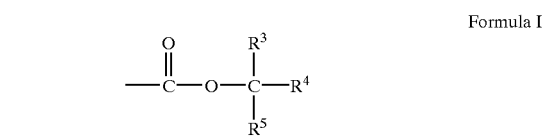

Formula I where $R^3$, $R^4$, and $R^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals $R^3$, $R^4$, and $R^5$ is other than hydrogen, and where at least one of the substituents $R^1$ and $R^2$ is a tert-butoxycarbonyl group of the Formula I; and Z is a substituent selected from the group consisting of —O—, —CO—, —S—, —S—S—, —SO$_2$—, —(CH$_2$)$_m$—, —(CF$_2$)$_m$ with m=1 to 10,

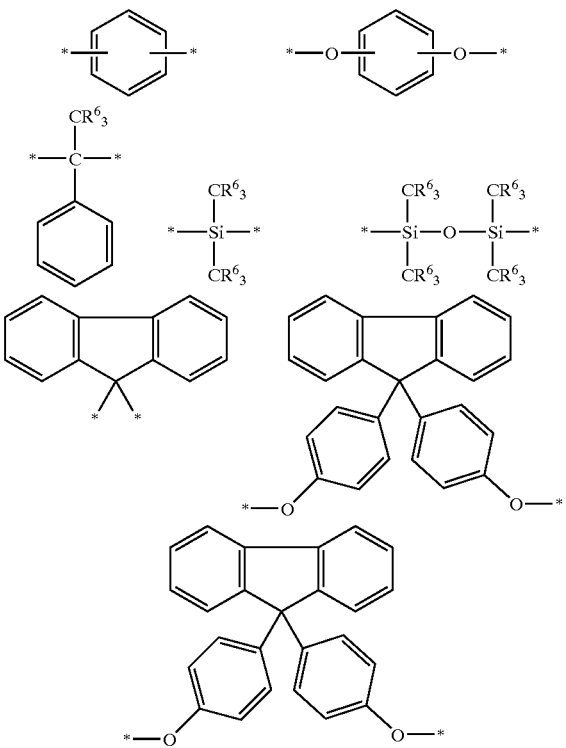

—C(CR$^7$$_3$)$_2$—, where $R^6$ is independently selected and denotes an alkyl radical having from 1 or 2 carbon atoms, hydrogen, and at least one of a halogen and a pseudohalogen, and where $R^7$ is independently selected and denotes an alkyl radical having from 1 to 2 carbon atoms, and at least one of a hydrogen, a F, a Cl, a Br, an I, and a pseudohalogen, and at least one $R^7$ is other than fluorine;

a poly-o-hydroxyamide including tert-butoxycarbonyl groups having a Formula I

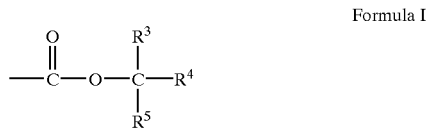

Formula I where $R^3$, $R^4$, and $R^5$ are substituents selected from the group consisting of: —H; —F; —(CH$_2$)$_n$—CH$_3$;

—(CF$_2$)$_n$—CF$_3$, where n is an integer from 0 to 10, provided that at least one of the radicals R$^3$, R$^4$, and R$^5$ is other than hydrogen, and where at least one of the substituents R$^1$ and R$^2$ is a tert-butoxycarbonyl group of the Formula I;

said tert-butoxycarbonyl groups being obtained, with at least one of a dicarboxylic acid or an activated derivative of a dicarboxylic acid, by condensing a bis-o-aminophenol derivative including:

a bis-o-aminophenol having a formula selected from the group consisting of Formula IIa and IIb

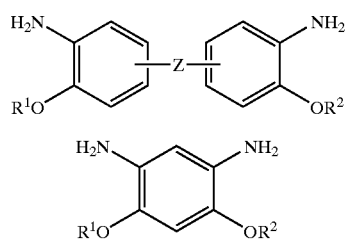

Formula IIa

Formula IIb where:
R$^1$ and R$^2$ are substituents independently selected from the group consisting of a hydrogen atom and a tert-butoxycarbonyl group having said Formula I; and Z is a substituent selected from the group consisting of a carbon-carbon single bond, a carbon-carbon bond shared by said two phenyl groups carrying said amino group and one of said OR$^1$ group and said OR$^2$ group, a divalent alkyl radical having from 1 to 20 carbon atoms, a divalent aryl radical having from 6 to 20 carbon atoms, and a divalent aralkyl radical having an alkyl group; and a poly-o-hydroxyamide including tert-butoxycarbonyl groups having a Formula I

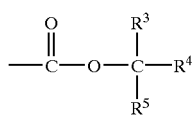

Formula I where R$^3$, R$^4$, and R$^5$ are substituents selected from the group consisting of: —H; —F; —(CH$_2$)$_n$—CH$_3$; —(CF$_2$)$_n$—CF$_3$, where n is an integer from 0 to 10, provided that at least one of the radicals R$^3$, R$^4$, and R$^5$ is other than hydrogen, and where at least one of the substituents R$^1$ and R$^2$ is a tert-butoxycarbonyl group of the Formula I;

said tert-butoxycarbonyl groups being obtained, with at least one of a dicarboxylic acid or an activated derivative of a dicarboxylic acid, by condensing a bis-o-aminophenol derivative including:

a bis-o-aminophenol having a formula selected from the group consisting of Formula IIa and IIb

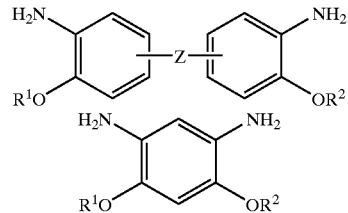

Formula IIb
where:
R$^1$ and R$^2$ are substituents independently selected from the group consisting of a hydrogen atom and a tert-butoxycarbonyl group having said Formula I; and Z is a substituent selected from the group consisting of —O—, —CO—, —S—, —S—S—, —SO$_2$—, —(CH$_2$)$_m$—, —(CF$_2$)$_m$ with m=1 to 10,

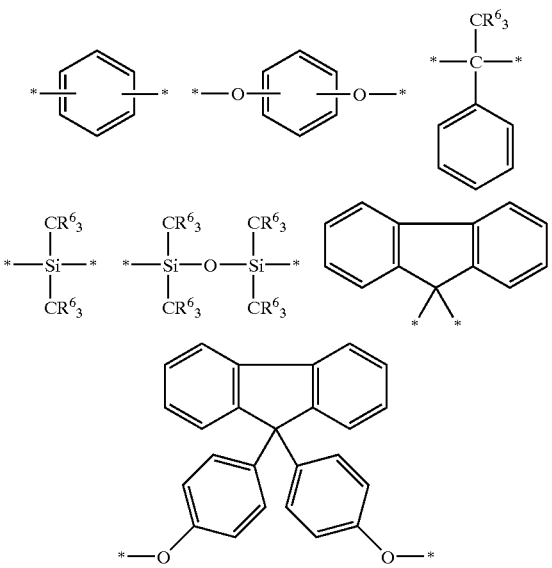

—C(CR$^7$$_3$)$_2$—, where R$^6$ is independently selected and denotes an alkyl radical having from 1 or 2 carbon atoms, hydrogen, and at least one of a halogen and a pseudohalogen, and where R$^7$ is independently selected and denotes an alkyl radical having from 1 to 2 carbon atoms, and at least one of a hydrogen, a F, a Cl, a Br, an I, and a pseudohalogen, and at least one R$^7$ is other than fluorine.

* * * * *